United States Patent [19]
Bonner

[11] Patent Number: 6,055,457
[45] Date of Patent: Apr. 25, 2000

[54] SINGLE PASS A-V LEAD WITH ACTIVE FIXATION DEVICE

[75] Inventor: Matthew D. Bonner, Plymouth, Minn.

[73] Assignee: Medtronic, Inc., Minneapolis, Minn.

[21] Appl. No.: 09/041,811

[22] Filed: Mar. 13, 1998

[51] Int. Cl.[7] .................................................. A61N 1/05
[52] U.S. Cl. ...................... 607/126; 607/123; 607/128
[58] Field of Search .................... 607/122–124, 607/126, 128, 130, 116, 119, 127; 600/375

[56] References Cited

U.S. PATENT DOCUMENTS

| | | |
|---|---|---|
| 4,091,817 | 5/1978 | Thaler . |
| 4,106,512 | 8/1978 | Bisping . |
| 4,136,703 | 1/1979 | Wittkampf . |
| 4,154,247 | 5/1979 | O'Neil . |
| 4,378,023 | 3/1983 | Trabucco ................................. 607/128 |
| 4,393,883 | 7/1983 | Smyth et al. . |
| 4,402,329 | 9/1983 | Williams . |
| 4,458,677 | 7/1984 | McCorkle, Jr. . |
| 4,497,326 | 2/1985 | Curry . |
| 4,721,118 | 1/1988 | Harris ..................................... 607/128 |
| 4,841,971 | 6/1989 | Hess . |
| 4,913,164 | 4/1990 | Greene et al. . |
| 5,030,204 | 7/1991 | Badger et al. . |
| 5,246,014 | 9/1993 | Williams et al. . |
| 5,318,525 | 6/1994 | West et al. . |
| 5,476,499 | 12/1995 | Hirschberg ............................. 607/123 |
| 5,484,407 | 1/1996 | Osypka . |
| 5,487,757 | 1/1996 | Truckai et al. . |
| 5,514,174 | 5/1996 | Heil, Jr. et al. ....................... 607/128 |
| 5,545,200 | 8/1996 | West et al. . |
| 5,571,162 | 11/1996 | Lin ......................................... 607/126 |
| 5,584,873 | 12/1996 | Shoberg et al. . |
| 5,628,778 | 5/1997 | Kruse et al. . |
| 5,628,779 | 5/1997 | Bornzin et al. . |
| 5,693,081 | 12/1997 | Fain et al. ............................. 607/126 |
| 5,871,532 | 2/1999 | Schroeppel ............................ 607/128 |

OTHER PUBLICATIONS

U.S. Patent Application, Ser. No. 08/846,008, filed by Ries et al. for a Medical Lead Connector System, on Apr. 25, 1997.

*Primary Examiner*—Kennedy J. Schaetzle
*Attorney, Agent, or Firm*—Reed A. Duthler; Harold R. Patton

[57] ABSTRACT

An implantable pacing lead system for pacing a patient's heart, including a delivery catheter and a lead delivered by the delivery catheter. The lead takes the form of a single non-diverging filament having a proximal end and a distal end and carries an electrode mounted to a distal portion of the lead body. An active fixation device is mounted fixedly to, and extends laterally from, the lead body proximal to and longitudinally spaced from the electrode. During advancement of the lead through the vasculature the active fixation device is located within the delivery catheter. At the point of desired location of the active fixation device, it is advanced out of the delivery catheter and engaged with heart tissue. The lead body has greater torsional rigidity proximal to the active fixation device than distal to the active fixation device.

28 Claims, 11 Drawing Sheets

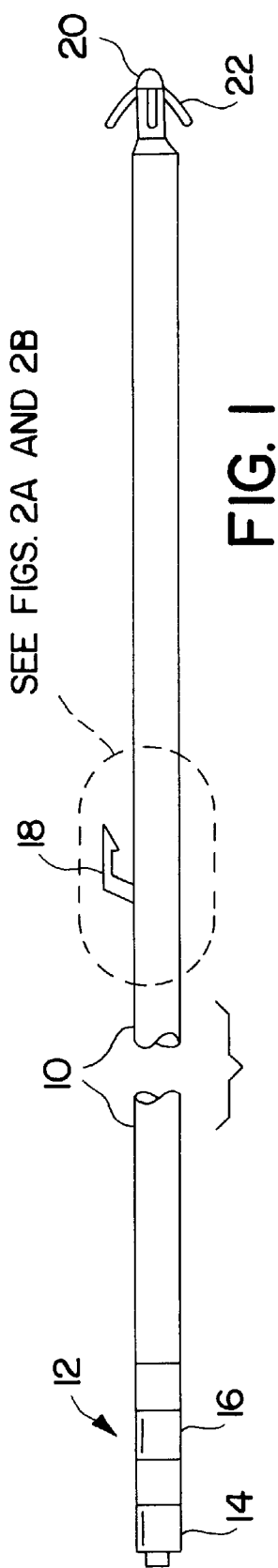
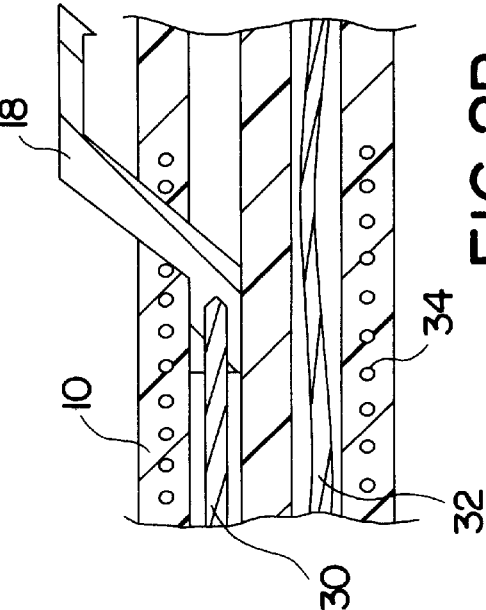
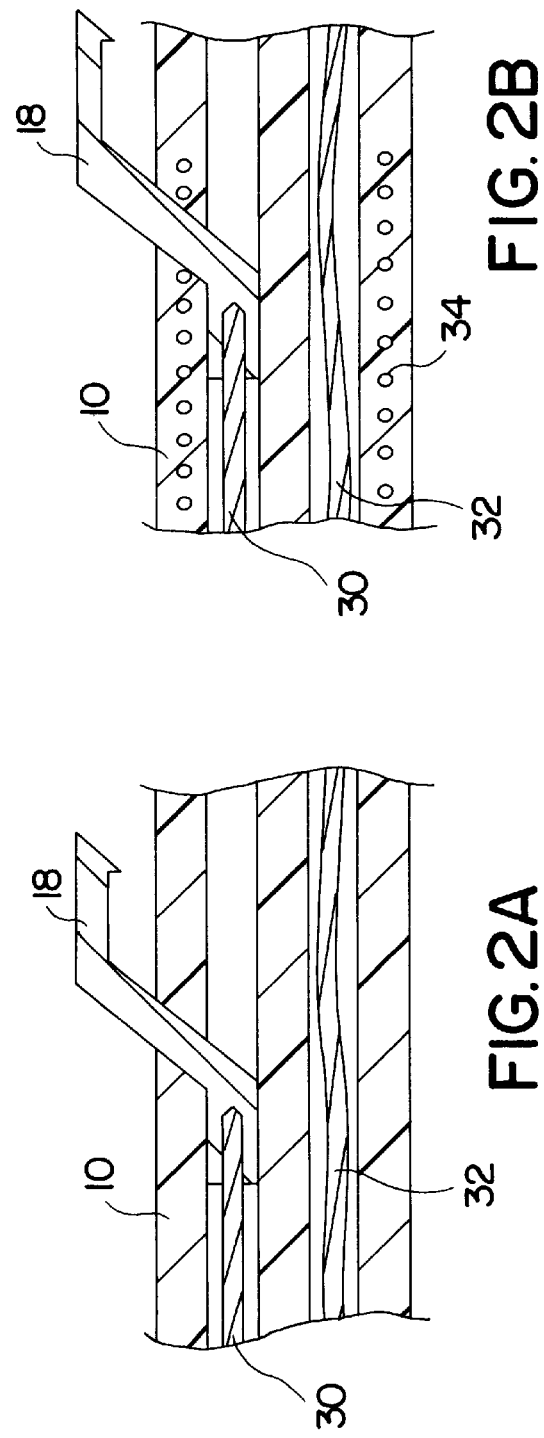
FIG. 1
FIG. 2A
FIG. 2B

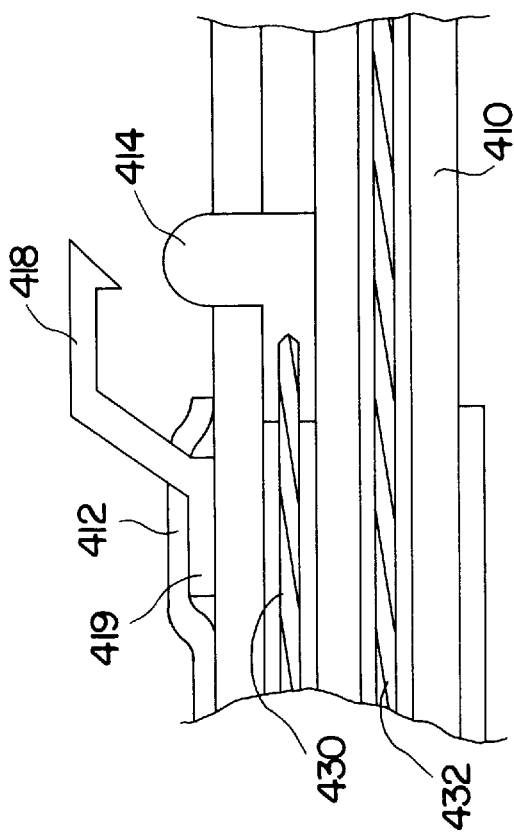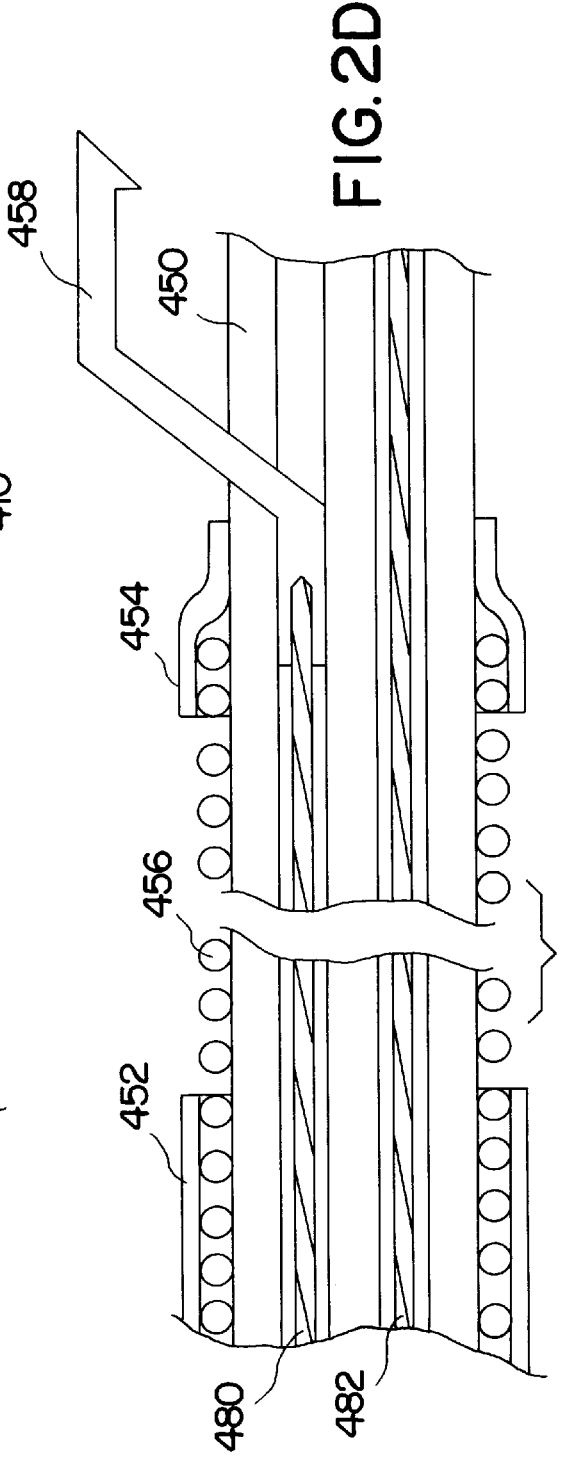

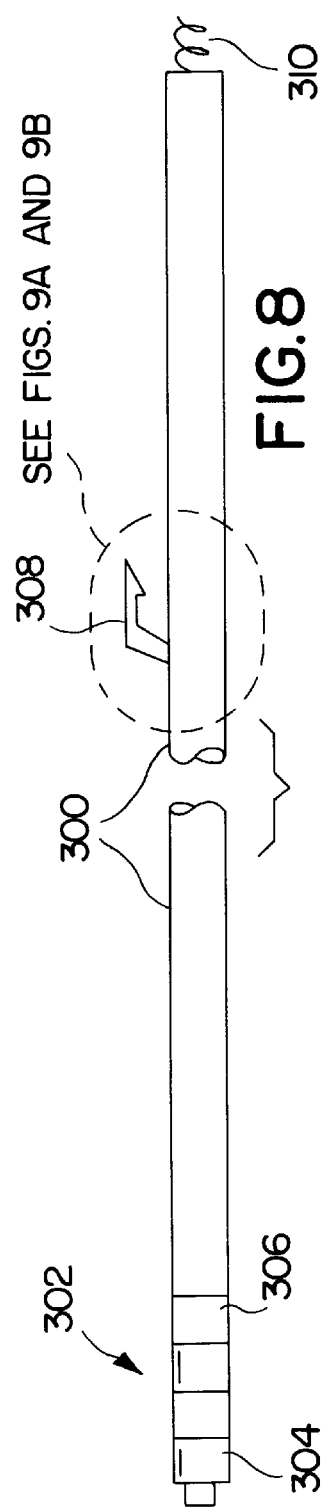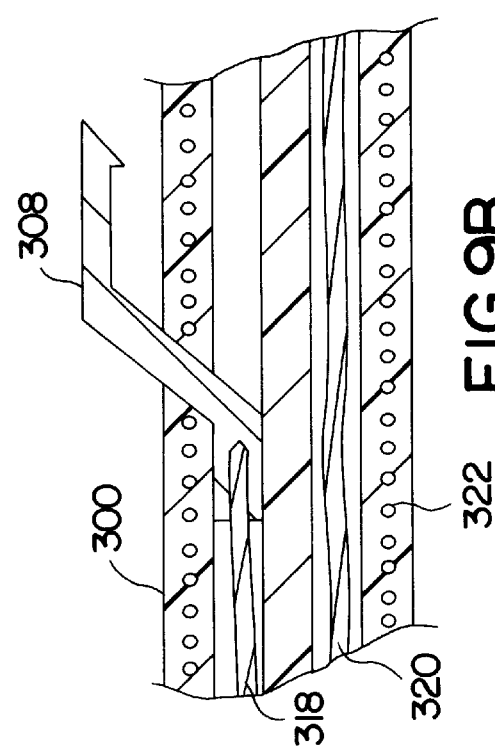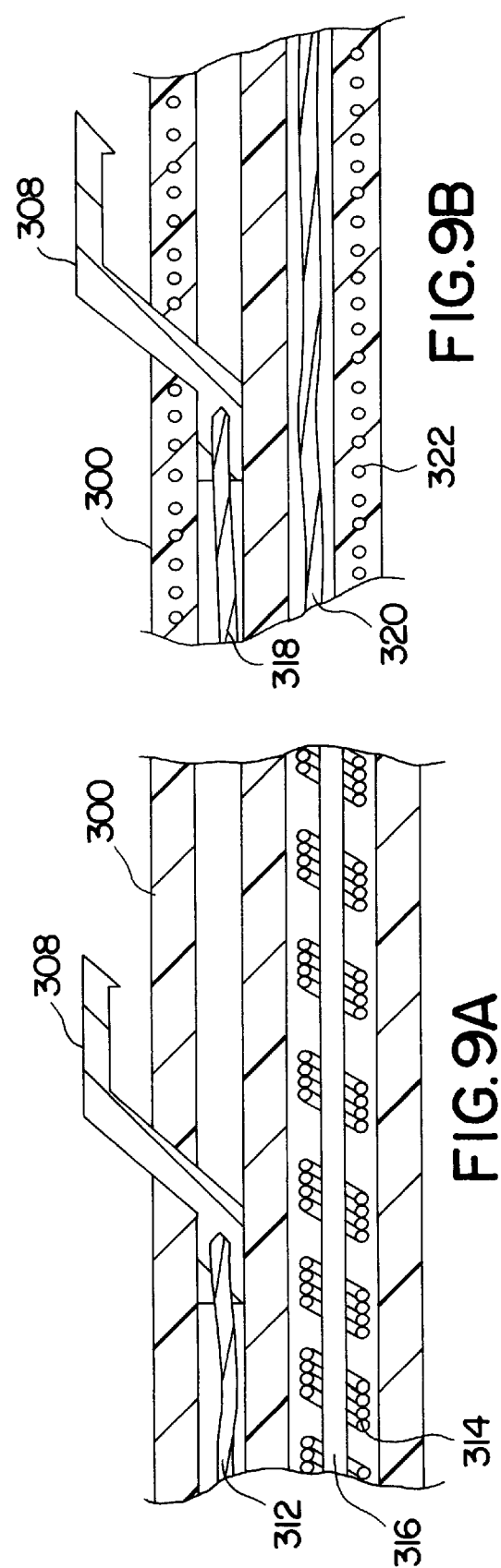

SINGLE PASS A-V LEAD WITH ACTIVE FIXATION DEVICE

BACKGROUND OF THE INVENTION

The present invention relates to implantable pacing leads generally and more particularly to implantable single pass A-V leads.

Over the years, there have been numerous proposals for single pass leads which can pace and sense in both the atrium and ventricle. As a practical matter, however, the single pass A-V leads available correspond generally to those illustrated in U.S. Pat. No. 4,091,817 issued to Thaler and include atrial electrodes which are in general only effective for sensing atrial depolarizations rather than pacing the atrium. The problem with single pass A-V leads has been the difficulty of providing a workable lead which reliably fixes an atrial pacing electrode adjacent atrial tissue without producing a lead which is unduly large in cross-section or unduly complex in manufacture or use. Examples of single pass A-V leads include leads in which the lead body is pre-formed to display a bend to urge an electrode into contact with the atrial wall. Such leads include those disclosed in U.S. Pat. No. 4,154,247 issued to O'Neill, U.S. Pat. No. 5,628,778, issued to Kruse et al. and U.S. Pat. No. 5,628,779 issued to Bornzin et al. An alternative approach has been to provide a lead in which the atrial lead is advanced out of the ventricular lead or conversely that the ventricular lead is advanced out of the atrial lead, the atrial lead being pre-curved in order to locate it in a desired position. Such leads are disclosed in U.S. Pat. No. 4,136,703 issued to Wittkampf, U.S. Pat. No. 4,458,677 issued to McCorkle et al and U.S. Pat. No. 4,393,883 issued to Smyth.

As an alternative to pre-forming the lead body or a portion thereof to urge the atrial electrode into contact with the atrium, it has also been suggested to provide an active fixation device in conjunction with the atrial electrode in order to maintain the atrial electrode in its desired location. Such leads are disclosed in U.S. Pat. No. 4,402,329 issued to Williams and to U.S. Pat. No. 4,497,326 issued to Curry. In such designs, the fixation device is typically fabricated in such a fashion that it can be located within the lead body during passage of the lead through the vascular system to prevent it from snagging on body tissue. In the Curry and Williams patents, this can be accomplished by providing a socket for receiving the atrial active fixation device within the lead body during its passage. An alternative embodiment is also disclosed in Curry wherein the active fixation device is withdrawable into the lead body during passage through the vascular system. Unfortunately, the mechanisms for shielding the atrial active fixation devices in the Williams and Curry patents substantially complicate both the manufacture of the lead and the implantation of the lead. The expedients adopted in these patents typically also produce a lead body of increased thickness as compared to two individual leads, passed down the same vein.

SUMMARY OF THE INVENTION

The present invention provides a single pass A-V lead with an atrial active fixation device, having substantially simplified structure as compared to previous such leads. In a lead according to the present invention, the atrial fixation device is mounted fixedly to a non-diverging lead body generally taking the form of a single, generally straight filament. The fixation device takes the form of a barb or hook extending laterally of the lead body, intending to engage the tissue of the atrium or the superior vena cava. The fixation device may serve as a pacing electrode or may be located adjacent a pacing electrode. The distal end of the lead carries an additional pacing electrode which may take the form of any conventional pacing electrode including both passive fixation electrodes such as a tined electrodes and active fixation electrodes such as screw-in electrodes.

The overall diameter of the lead body is kept small by virtue of the fact that it need only carry conventional conductor lumens and need not include any mechanisms for sliding or advancing the atrial or ventricular lead with respect to one another and similarly need not include any additional structures for shielding or guarding the atrial active fixation device during passage through the vascular system. Instead, the lead is advanced to its desired location by means of a guide catheter or cannula, preferably a deflectable or steerable guide catheter or cannula. The ventricular electrode is first located in its desired location within the apex of the right ventricle, followed by withdrawal of the guide catheter to a point adjacent to the atrial active fixation device. The guide catheter is then employed to position the atrial active fixation device at a desired location within the atrium. By advancing the guide catheter together with the lead toward the desired location, the atrial electrode, which may be the active fixation device or may be located adjacent the active fixation device, can be positioned without the necessity of a longitudinal element within the lead providing axial strength such as a stylet, coiled conductor or other structure. The ability to so position the electrode in turn reduces the required overall diameter of the lead.

In some preferred embodiments, the lead body is constructed to allow for torque transfer along the length of the lead between the proximal end of the lead and the atrial active fixation electrode so that it may be positioned rotationally in an appropriate position to engage the atrial tissue. In other embodiments, the guide catheter may be provided with a mechanism for engaging the active fixation device so that it may be employed to appropriately position the active fixation device for engagement with atrial tissue.

BRIEF DESCRIPTION OF THE DRAWINGS

FIG. 1 is a plan view of a first embodiment of a lead according to the present invention.

FIGS. 2A, 2B, 2C and 2D are alternative embodiments of internal structure appropriate for use in constructing leads according to the invention.

FIG. 8 is a plan view of an additional alternative embodiment of a lead according to the present invention.

FIGS. 9A and 9B are cross-sections through alternative embodiments of the lead illustrated in FIG. 8, illustrating internal structures appropriate for use in constructing a lead according to FIG. 8.

DETAILED DESCRIPTION OF THE PREFERRED EMBODIMENTS

Figures 3, 4A, 4B:
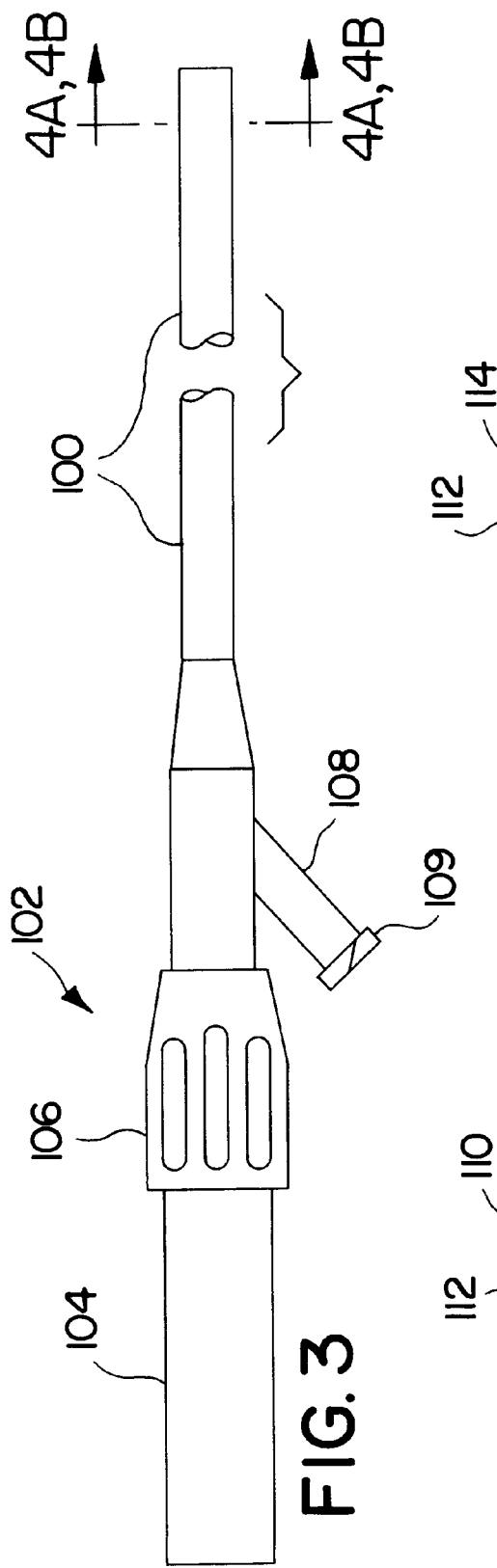
FIG. 3 is a plan view of a deflectable guide catheter of the sort appropriate for use in conjunction with a lead according to the present invention.
FIGS. 4A and 4B are cross-sections through the alternative embodiments of the guide catheter illustrated in FIG. 3.

FIG. 1 is a plan view of a first general type of a lead embodying the present invention. The lead is provided with an elongated insulative lead body 10 which carries two elongated conductors therein. At the proximal end of the lead is located a connector assembly 12 which carries two connector rings 14 and 16. Connector assembly 12 may correspond to that illustrated in allowed U.S. application Ser. No. 08/846,008, filed by Ries et al. for a Medical Lead Connector System, on Apr. 25, 1997, now U.S. Pat. No. 5,843,141, incorporated herein by reference in its entirety, with the exception that it includes only two electrical connector rings rather than four. At the proximal end of the lead is located a pacing/sensing electrode 20, along with adjacent pliant tines 22 which serve to maintain the electrode 20 in a desired location in the right ventricular apex. An active fixation electrode 18 taking the form of a hook or barb is located proximally to electrode 20, spaced from electrode 20 a distance sufficient to locate electrode 18 in the right atrium or superior vena cava of a patient's heart when electrode 20 is located in the right ventricle, and spaced so that when electrodes 18 and 20 are so located, that the lead exhibits substantial slack between the two electrodes. Electrode 18 is coupled to one of the two conductors within lead body 10, which is in turn coupled to connector ring 16. Electrode 20 is coupled to the other of the two conductors within the lead body 10 which in turn is coupled to connector ring 14.

While the lead illustrated in FIG. 1 includes only a single electrode 18 for pacing and sensing in the atrium and a single electrode 20 for pacing and sensing in the ventricle, it is within the scope of the invention to add additional electrodes to the lead to provide for bipolar sensing and pacing in the atrium and/or ventricle. It is also within the scope of the invention to add a cardioversion/defibrillation electrode or physiologic sensor or other component to the lead.

FIG. 2A illustrates a cross-section through the lead illustrated in FIG. 1 in the vicinity of active fixation electrode 18. In this embodiment of the invention, the lead body 10 takes the form of a bitumen tube formed of a biocompatible plastic such as polyurethane or silicone rubber, carrying two elongated stranded conductors which may correspond, for example, to those described in U.S. Pat. No. 5,584,873 issued Shoberg et al. or U.S. Pat. No. 5,246,014, issued to Williams et al. both incorporated herein by reference in their entireties. Active fixation electrode 18 takes the form of a barb or hook extending laterally from the side of lead body 10 and coupled to stranded conductor 30. Stranded conductor 32 extends to the distal end of the lead and is coupled to tip electrode 20.

FIG. 2B illustrates a cross section through an alternative embodiment of a lead corresponding to FIG. 1, in the vicinity of active fixation electrode 18. In this embodiment, the lead is similarly provided with stranded conductors 30 and 32, but the lead body in addition is provided with a reinforcing braid or mesh 10 which provides for torsional rigidity of the lead extending to the vicinity of active fixation electrode 18. The provision of the reinforcing braid 34 allows for rotation of electrode 18 in response to rotation of connector assembly 12 (FIG. 1) at the proximal end of the lead. This in turn assists in positioning the electrode appropriately for engaging atrial tissue as will be discussed below.

FIG. 2C illustrates a cross-section through an alternative embodiment of the lead according to the present invention employing an active fixation device which itself does not function as an electrode but instead is employed to anchor an adjacent electrode against heart tissue. The lead body 410 is a bitumen lead body carrying first and second stranded conductors 430 and 432. Stranded conductor 432 is coupled to an electrode 414 which exits the side of lead body 410, so that it may lay along side heart tissue. Active fixation 418 is a barb having the same configuration as the active fixation electrodes illustrated in FIGS. 1, 2A and 2B. Active fixation device 14, however, is not coupled to any conductors, but is instead mounted to the exterior of the lead body 410, and serves solely to anchor the lead body to heart tissue adjacent electrode 414. In the particular embodiment illustrated, active fixation device 418 is provided with an enlarged, flattened base portion 19 which is mounted to lead body 410 by means of a plastic sheath 412, and optionally by means of adhesives. Any appropriate mechanism for mounting the fixation device 418, of course, may be employed.

FIG. 2D is a cross-section through an additional alternative embodiment of a lead according to the present invention. In this embodiment, the lead body 450 takes the form of a bitumen tube provided with first and second stranded conductors 480 and 482. Conductor 482 is coupled to active fixation electrode 458, which is intended to be inserted into heart tissue in the atrium or superior vena cava. In this embodiment, the lead is provided with an elongated cardioversion/defibrillation electrode 456, for location in the superior vena cava and/or right atrium of the heart. In a preferred embodiment, cardioversion/defibrillation electrode 456 may simply be a continuation of a coiled conductor mounted around lead body 450, and insulated over the majority of its length by insulative sheath 452. In such an embodiment the coiled conductor serves to provide enhanced torque transfer along the length of the lead body to the vicinity of the active fixation device 458. Alternatively, the lead may be provided with a third conductor mounted within lead 450 and coupled to a separately formed coil electrode 456. The distal end of the cardioversion/defibrillation electrode 456 is anchored in place against lead body 450 by insulative sheath 454. As an additional alternative, active fixation device 458 may simply serve to anchor the lead adjacent the distal end of cardioversion/defibrillation electrode 456, and need not serve as an electrode.

FIG. 3 is a plan view of a deflectable guide catheter which may be employed to deliver the leads according to FIGS. 1, 2A, 2B, 2C and 2D. The deflectable catheter may correspond generally to that illustrated in U.S. Pat. No. 5,484,407 issued to Osypka and incorporated herein by reference in its entirety. Alternatively, a deflectable guide catheter according to U.S. Pat. No. 5,030,204 issued to Badger et al may be substituted. The catheter is provided with a handle 104 which carries a rotatable knob 106 which in turn operates to push or pull a deflection wire located within the catheter body which in turn causes the distal portion of the catheter body 100 to assume a curved configuration. For purposes of the present invention it should be assumed that the knob 106 operates to retract a pull wire which is eccentricly located within the catheter body 100 and which on retraction causes the distal portion of the catheter body 100 to curve such that the pull wire is located on the interior of the curve so formed. This conventional deflection mechanism may, within the scope of the invention, be replaced by other more complex deflection mechanisms as disclosed in U.S. Pat. No. 5,545,200 issued to Tracy et al., U.S. Pat. No. 5,487,757 issued to Truckai et al. or U.S. Pat. No. 5,318,525 issued to West et al. which provide for the ability to control the deflection of the guide catheter in three dimensions. Additional alternative guide catheter designs may include stylet steered catheters, nested tube catheters or in some cases pre-formed fixed curve catheters. A Y-fitting 108 is provided on the handle 104 of the catheter allowing for insertion of the lead into the catheter body, via luer lock 109.

FIG. 4A illustrates a cross-sectional view through a first embodiment of a guide catheter corresponding generally to that illustrated in FIG. 3. In this embodiment, the guide catheter is of conventional construction including a tubular plastic catheter body 100, an internal lumen 114 through which the lead might pass, and an eccentricly located pull wire 112. In this embodiment, the guide catheter is in addition provided with an elongated slot 110 extending along the lumen 114 of the catheter, providing a passage way for active fixation electrode 15. The embodiment illustrated in FIG. 4A is believed particularly useful in conjunction with a lead constructed according to the embodiment illustrated in FIG. 2A, which in some cases may have relatively little in the way of torsional rigidity between the connector assembly 12 at the proximal end of the lead and the active fixation electrode 18. By means of slot 100, the rotational orientation of the active fixation electrode 18 is predetermined. Because tension wire 112 is located closely adjacent slot 110, the active fixation electrode 18 on emerging from the guide catheter will be positioned on the interior of the curve induced by pull wire 112 which in turn assists its engagement with atrial tissue as discussed below.

FIG. 4B illustrates an alternative embodiment in which the catheter body 100 is provided with a simple circular lumen 114, sized to be large enough to allow passage of the lead body including the active fixation electrode 18, along its length. In this embodiment, the lead is free to rotate with respect to the deflectable catheter body 100. This embodiment is believed better suited for use in conjunction with the embodiment of the lead illustrated in FIG. 2B, in that the rotational alignment of the electrode 18 relative to the guide catheter body 100 may be controlled by rotating the proximal end of the lead to place active fixation electrode 18 in its desired position for engaging the tissue of the atrium.

Figure 5:
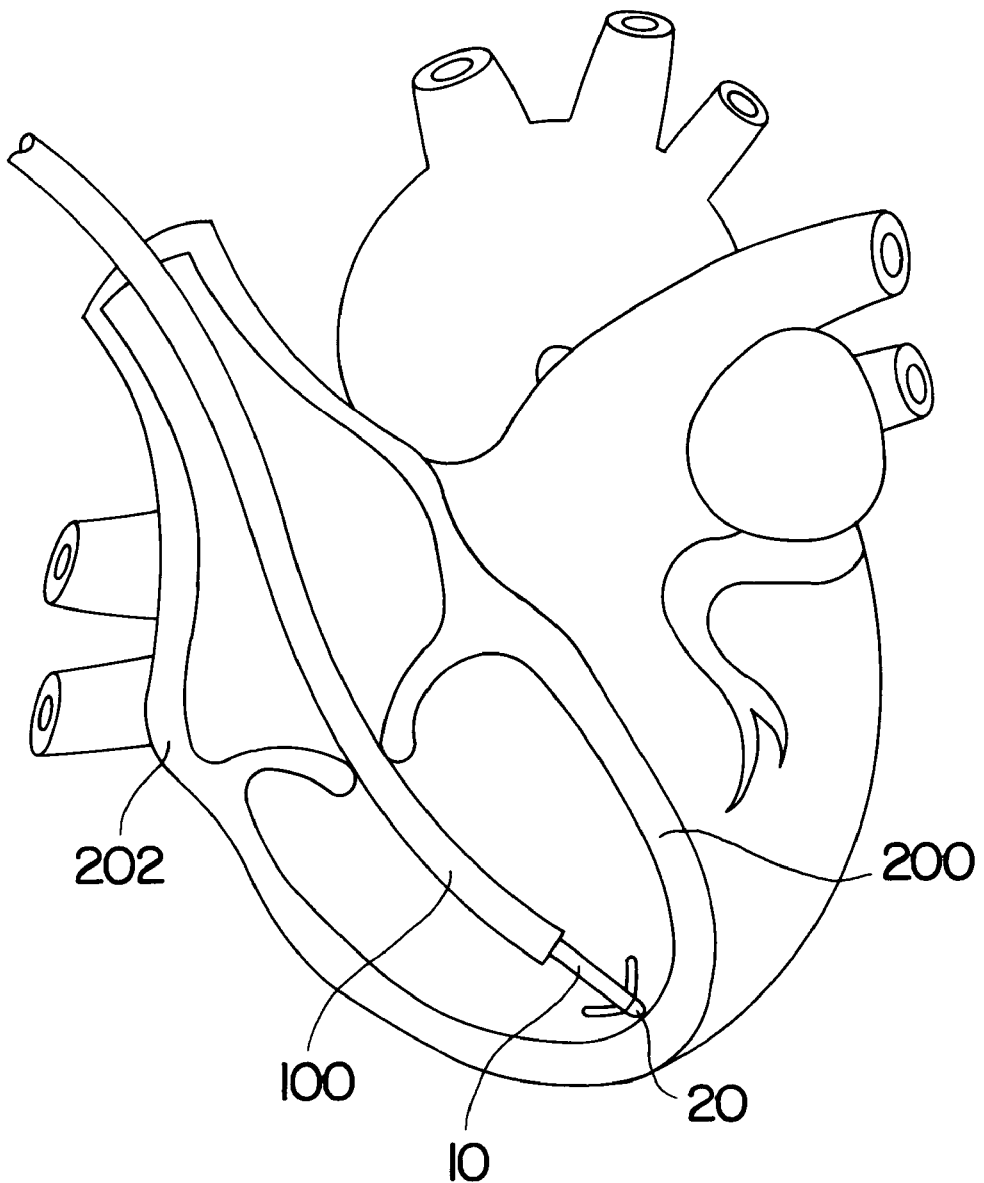
FIGS. 5 through 7 are a sequence of drawings illustrating the implantation of a lead according to the present invention in a human heart.

FIG. 5 illustrates the first stage of implantation of a lead according to the present invention. In this view, the distal portion of lead body 10 has been advanced out of guide catheter 100 allowing placement of tip electrode 20 in its desired location in the right ventricle. Guide catheter 100 is then withdrawn proximally until its distal end is located in the atrium 200 and 2 of the heart.

Figure 6:
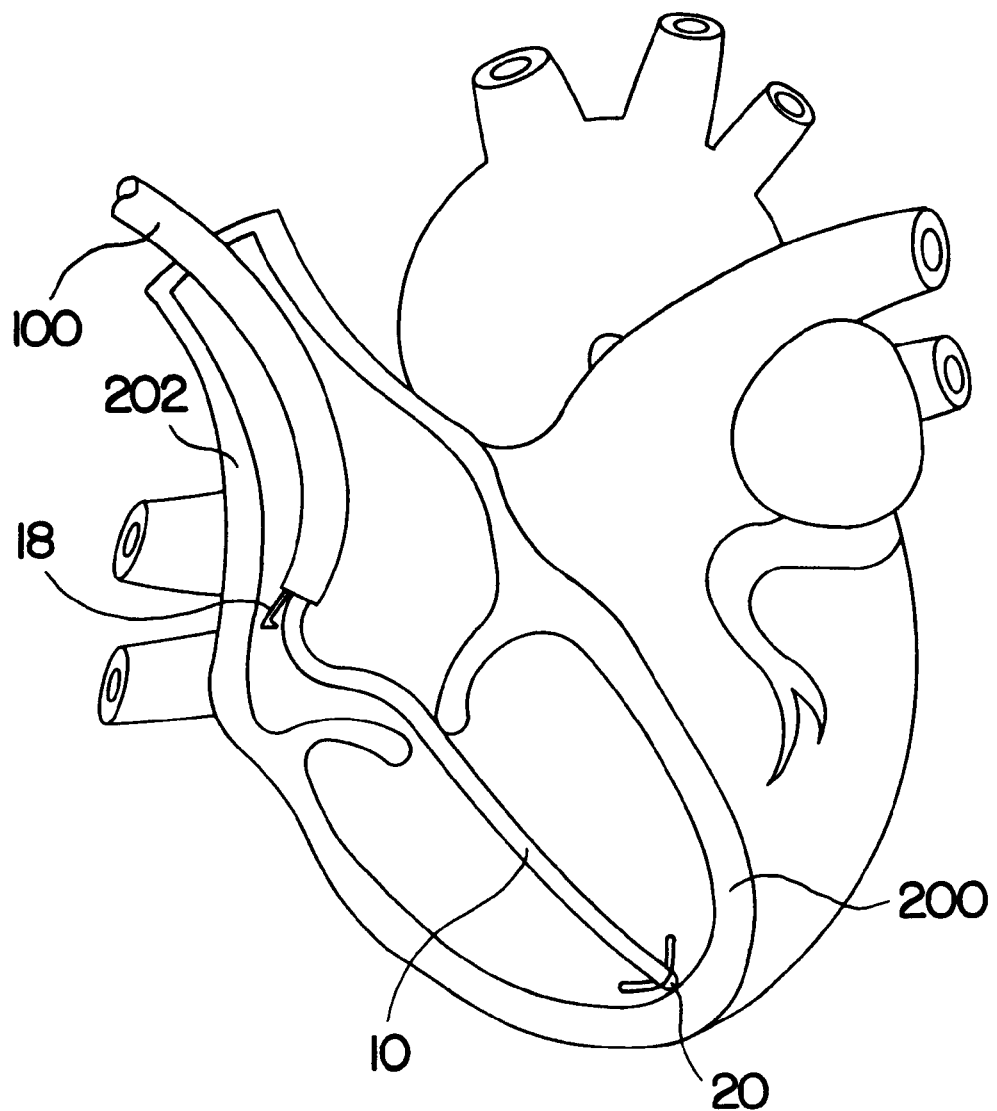

FIG. 6 illustrates an intermediate step in the location of the lead. In this view, guide catheter 100 has been withdrawn proximally until active fixation electrode 18 has emerged to some extent from the distal end of the catheter. The tension wire in the guide catheter has been retracted causing it to assume a curve which assists in directing fixation electrode 18 adjacent the wall of atrium 200. The guide catheter and the lead may be advanced together as a unit in order to seat active fixation electrode 18 in atrial tissue at a desired location or the lead may be advanced relative to the catheter.

If the embodiment of the guide catheter corresponds to that illustrated in FIG. 4A, the rotational orientation of fixation electrode 18 with regard to the guide catheter body is fixed. In this case, the electrode 18 will always be located adjacent the interior of the curve formed in guide catheter body 100 as illustrated, which in turn places it in an appropriate location for engagement of atrial tissue to when the guide catheter 100 is curved. If the guide catheter embodiment of FIG. 4B is employed, it is preferable to employ the lead embodiment illustrated in FIG. 2B, with the lead being rotated within the guide catheter so that electrode 18 is appropriately positioned for location in the atrial tissue. It should be noted in conjunction with this procedure that the termination of the reinforcing braid 34 in the vicinity of active fixation electrode 18 results in the lead body 10 between the two electrodes having a reduced degree of torsional rigidity, reducing the likelihood that any torsional forces produced by twisting of the lead body can cause dislodgment of either electrode 18 or 20.

Figure 7:
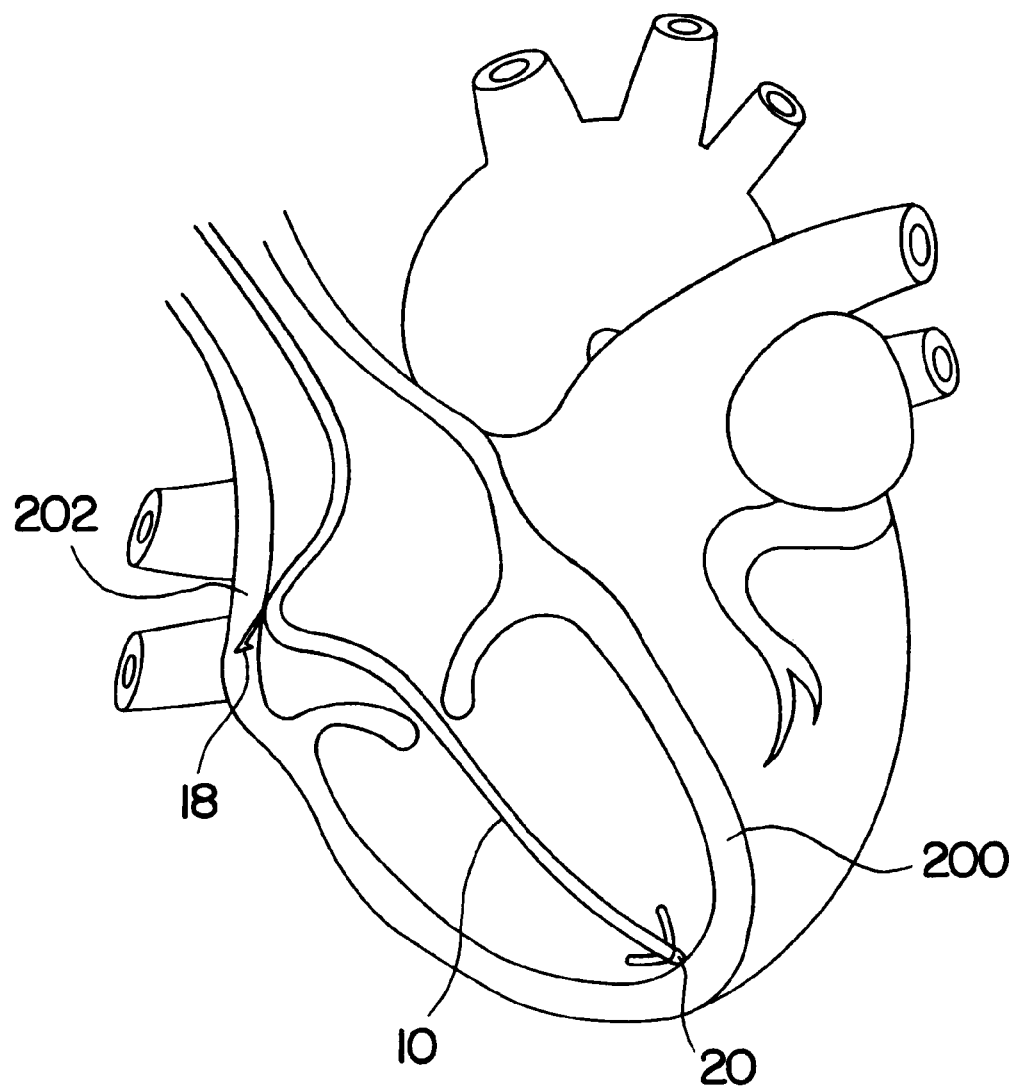

FIG. 7 illustrates the lead as implanted with electrode 20 located in the apex of the right ventricle 200 and electrode 18 embedded in the wall of atrium 202. The lead body 10 has sufficient length between electrode 18 and electrode 20 to display significant amount of slack to prevent tension applied between electrodes 18 and 20 from dislocating electrodes after implant.

FIG. 8 illustrates an alternative type of lead embodying the present invention. The lead is provided with an elongated insulative lead body 300 which carries therein two elongated conductors. At the proximal end of the lead is located connector assembly 302 which is provided with connector rings 306 and 304. An active fixation electrode 308 is located on the lead body spaced from a distal helical active fixation electrode 310 a distance sufficient to allow for the lead body 300 to exhibit slack when the electrode 308 is placed in the wall of the right atrium and the active fixation electrode 310 is placed in the right ventricular apex. The connector assembly 302 corresponds to connector assembly 12 illustrated in FIG. 1. Helical electrode 310 is preferably a screw-in electrode mounted to lead body 300, and rotated in the tissue by one of the two mechanisms illustrated in conjunction with FIGS. 9A and 9B below.

FIG. 9A illustrates a cross-sectional view through a lead corresponding to FIG. 8, illustrating a first alternative embodiment thereof. The lead body 300 takes the form of an elongated plastic bitumen tube carrying a first stranded conductor 312 coupled to active fixation electrode 308 and a second, coiled conductor 314 which is coupled to helical electrode 310. Extending through coiled conductor 314 is a screwdriver tipped stylet 316 which engages the electrode 310 at the distal end of the lead in the fashion described in U.S. Pat. No. 4,217,913 issued to Dutcher, so that torque applied to the distal end of the lead by stylet 316 may be employed to screw electrode 310 into the right ventricular apex. An additional alternative embodiment would be to employ a rotatable coiled conductor 314 coupled to a rotatable helical electrode 310 corresponding generally to that described in U.S. Pat. No. 4,106,512 issued to Bisping, incorporated herein by reference in its entirety. As illustrated, the lead body 300 itself has little torsional rigidity between active fixation electrode 308 and active fixation electrode 310, so that torsional forces applied between the two electrodes will not tend to dislocate either of the two electrodes, as described above in conjunction with the lead illustrated in FIGS. 1, 2A and 2B. Optionally, a reinforcing braid may be added to the lead body 300, corresponding to reinforcing braid 34 illustrated in FIG. 2B, facilitating rotation of electrode 308 relative to a guide catheter used to implant the lead. Implantation of the lead corresponds generally to that described in conjunction with the leads illustrated above, with the exception that the location of the active fixation electrode 310 will require rotation of the lead body as part of the positioning process, unless a rotatable coiled conductor is employed.

FIG. 9B illustrates an alternative embodiment of a lead corresponding to that illustrated in FIG. 8 in which the lead body 300 is formed of a bitumen tube provided with a reinforcing braid 322 extending along the entire length of the lead, allowing for torque transfer along the entire length of the lead. In this case, the lead is provided with two elongated stranded connectors 318 and 320 coupled to electrodes 308 and 310, respectively. In implanting this lead, torque is applied to electrode 310 by means of rotation of connector assembly 302.

Figure 10:
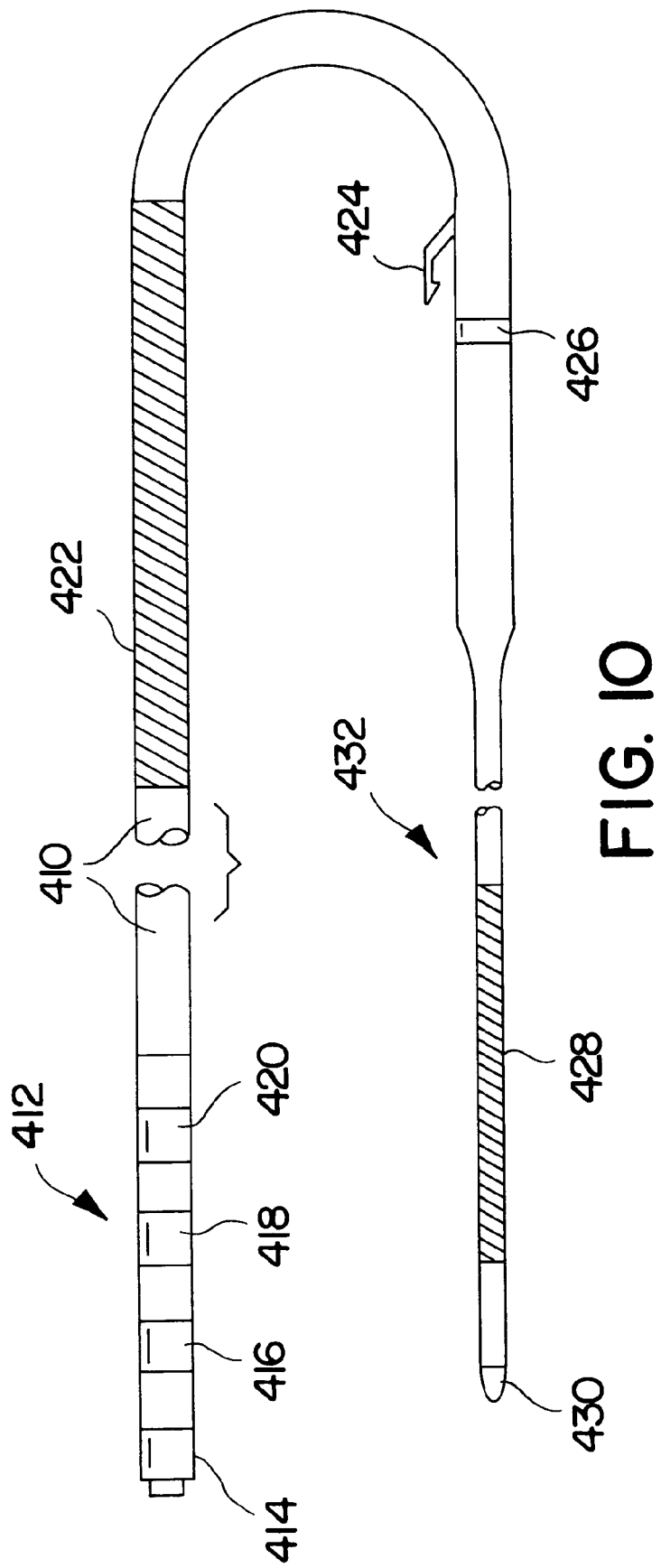
FIG. 10 is a plan view of a second additional alternative embodiment of a lead according to the present invention.

FIG. 10 is an illustration of a second alternative embodiment of a lead according to the present invention. In this embodiment the lead is provided with a quadrapolar in-line connector assembly 412 carrying four connector rings, 414, 416, 418 and 420, according to the above cited Ries et al. application. Connector assembly 412 is mounted at the proximal end of lead body 410, which in turn carries a first cardioversion/defibrillation electrode 422 intended for location in the right atrium/superior vena cava of a patient's heart, an atrial pacing/sensing electrode intended for location adjacent the tissue of the right atrium or superior vena cava, a ventricular cardioversion/defibrillation electrode 428 intended for location in the great cardiac vein adjacent the right ventricle and a ventricular pacing electrode 430 intended for location in the great cardiac vein adjacent the left ventricle. The distal portion 432 of the lead is of reduced diameter to facilitate placement in the coronary sinus/great vein of the patient's heart. Active fixation device 424 is provided adjacent atrial pacing electrode in order to anchor the electrode adjacent heart tissue. In the embodiment illustrated, active fixation device 424 is insulated and serves only to maintain electrode 426 in contact with tissue of the heart. However, active fixation device 424 may alternatively also be an electrode to provide for bipolar pacing and sensing. Similarly, in the embodiment illustrated it is envisioned that ventricular pacing/sensing electrode 430 will be used in conjunction with cardioversion/defibrillation electrode 428 to provide an integrated bipolar ventricular pacing/sensing electrode system. However, an addition to the electrode may of course be provided in order to provide a conventional bipolar ventricular pacing/sensing electrode system. If the distal portion 432 of the lead is reduced in length or the location of the electrodes thereon is varied, the lead may also be employed to position pacing and/or cardioversion electrodes adjacent the left atrium of the patient's heart.

Figure 11:
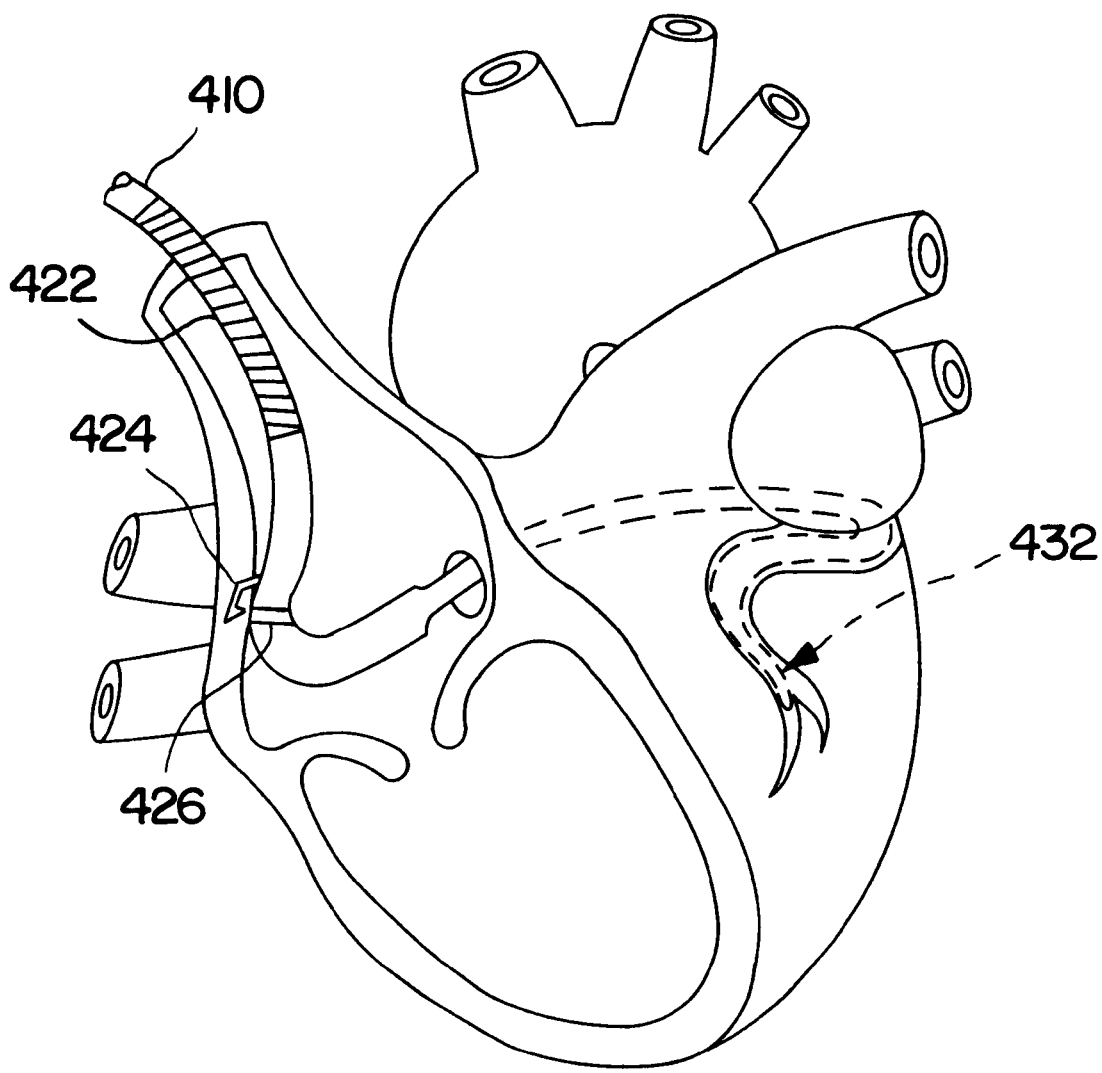
FIG. 11 is a drawing illustrating the implantation of a lead according to FIG. 10 in a human heart.

FIG. 11 illustrates the lead of FIG. 10 as implanted in a human heart. The distal portion 432 of the lead has been advanced into the coronary sinus/great vein of the heart so that the cardioversion/defibrillation electrode 428 and pacing electrode 430 are located adjacent the left ventricle. Active fixation device 424 maintains electrode 426 against the tissue of the right atrium or superior vena cava, with cardioversion/defibrillation electrode 422 located in the right ventricle or superior vena cava.

Figure 12:
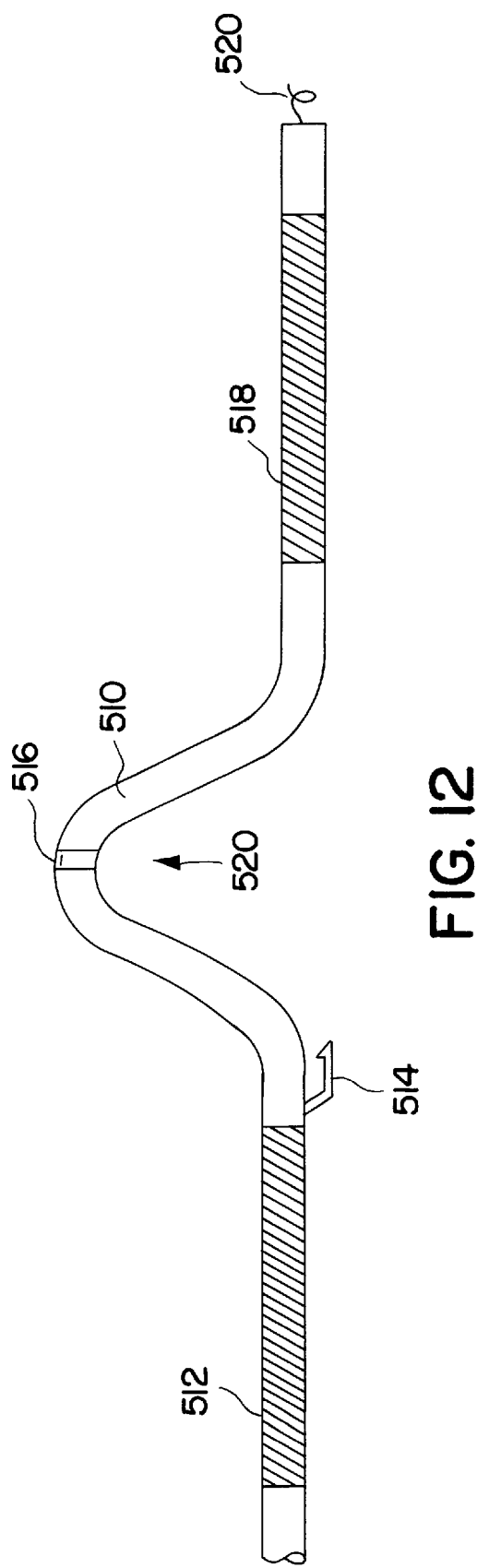
FIG. 12 is a plan view of a third additional alternative embodiment of a lead according to the present invention.

FIG. 12 illustrates a third alternative embodiment of a lead according to the present invention. Although not illustrated, the proximal end of the lead body carries a connector assembly as illustrated in FIG. 10, discussed above. In this embodiment, the lead body 510 carries a cardioversion/defibrillation electrode 512 intended for location in the right atrium/superior vena cava of a patient's heart, an atrial pacing electrode 516 intended for location in the right atrium or superior vena cava of the patient's heart, a ventricular cardioversion/defibrillation electrode 518 and a helical screw-in electrode 520. In this embodiment, fixation device 514 does not function as an electrode but simply serves to maintain the lead located adjacent tissue of the right atrium or superior vena cava of the patient's heart. The lead body 510 is provided with a pre-formed curve 520, along which electrode 516 is located. The curve is configured to maintain electrode 516 adjacent atrial tissue while active fixation device 514 is embedded in the tissue of the patient's right atrium or superior vena cava, providing a support for the curved section of the lead.

Figure 13:
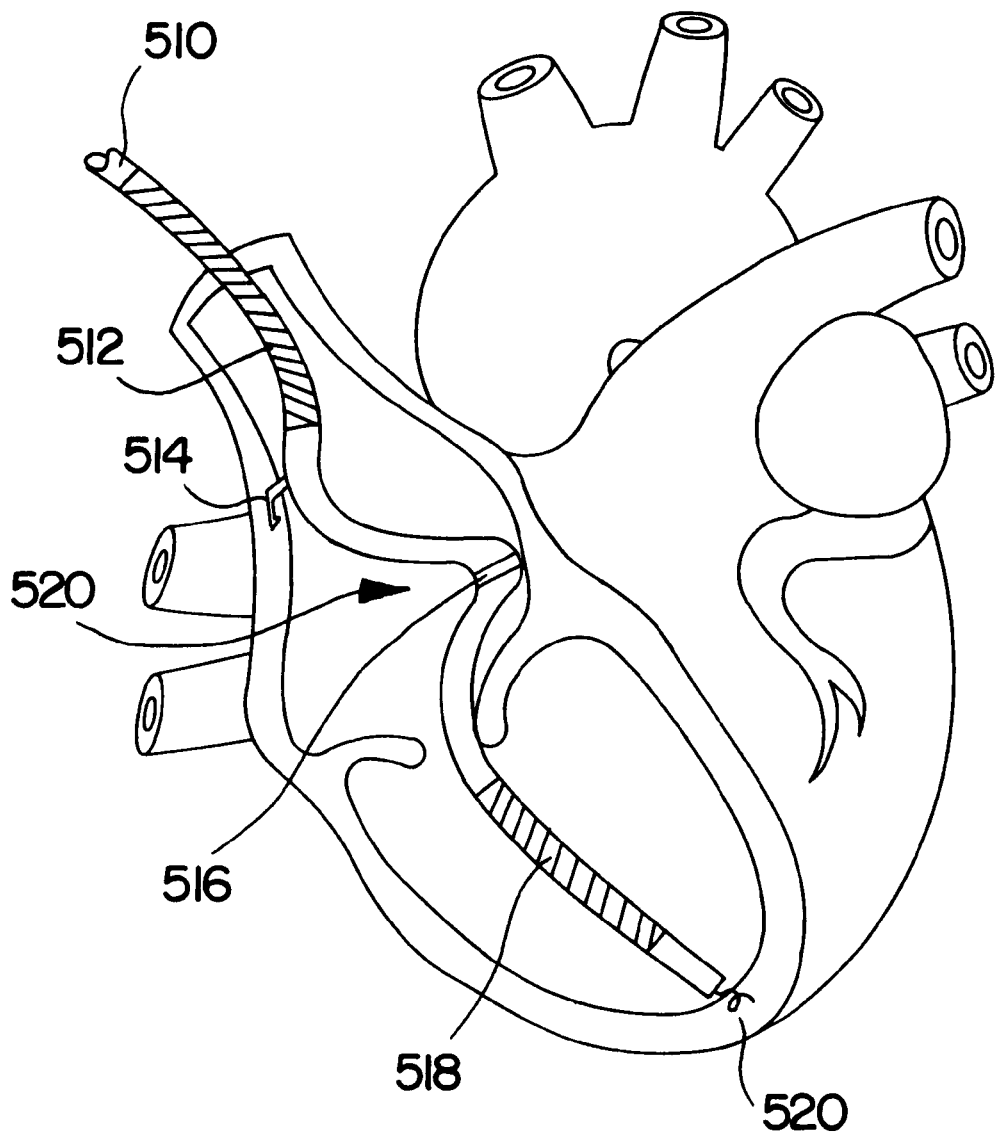
FIG. 13 is a drawing illustrating the implantation of a lead according to FIG. 12 in a human heart.

FIG. 13 shows the lead of FIG. 12 as implanted in a human heart. The helical ventricular electrode 520 is shown embedded in the right ventricular apex with cardioversion/defibrillation electrode 518 located within the right ventricle. Active fixation device 514 is embedded in the tissue of the right atrium or superior vena cava such that the pre-formed curved 520 urges electrode 516 is urged into contact with the wall of the right atrium to allow for atrial pacing and sensing.

The above described embodiments of a lead according to the present invention provide for the inclusion of a wide variety of electrode types and locations. The embodiments illustrated above have in common a catheter delivered lead having a fixedly mounted active fixation device extending laterally of the body of a lead and employed to maintain that portion of the lead body adjacent the tissue of a patient's atrium or superior vena cava, the lead body extending distally from the active fixation device and carrying one or more electrodes intended for location in or adjacent the chamber other than the right ventricle of the patient's heart. Within this general context, it is believed that a substantial variety of lead configurations may usefully benefit from the present invention. The above illustrated embodiments therefore should be considered as exemplary, rather than limiting, with regard to the claims which follow.

In conjunction with the above specification, we claim:

1. An implantable pacing lead system for pacing a patient's heart, comprising:
   a delivery catheter;
   an elongated insulative lead body locatable in said delivery catheter and taking the form of a single non-diverging filament having a proximal end and a distal end;
   a first electrode mounted to a distal portion of the lead body; and
   a second electrode which is an active fixation device mounted fixedly to and extending laterally from the lead body proximal to the first electrode and longitudinally spaced from the first electrode, locatable within the delivery catheter;
   wherein said lead body comprises means for providing torsional rigidity extending between said active fixation device and the proximal end of the lead body and wherein said lead has greater torsional rigidity proximal to said active fixation device than distal to said active fixation device.

2. A lead system according to claim 1 wherein the first electrode is a pacing electrode.

3. A lead system according to claim 1 wherein the first electrode is a cardioversion/defibrillation electrode.

4. A lead system according to claim 1 wherein said delivery catheter comprises means for engaging said active fixation device.

5. A lead system according to claim 4 wherein said engaging means comprises a groove formed in a distal portion of said delivery catheter.

6. An implantable pacing lead system for pacing a patient's heart, comprising:

a delivery catheter;

an elongated insulative lead body locatable in said delivery catheter and taking the form of a single non-diverging filament having a proximal end and a distal end;

a first electrode mounted to a distal portion of the lead body; and an active fixation device mounted fixedly to and extending laterally from the lead body proximal to the first electrode and longitudinally spaced from the first electrode, locatable within the delivery catheter, wherein said delivery catheter is a deflectable catheter;

wherein said lead body comprises means for providing torsional rigidity extending between said active fixation device and the proximal end of the lead body and wherein said lead has greater torsional rigidity proximal to said active fixation device than distal to said active fixation device.

7. A lead system according to claim 6 wherein said delivery catheter is deflectable to define a first curve having an interior and wherein said catheter is provided with means for locating said active fixation device along the interior of said curve.

8. A lead system according to claim 7 wherein said locating means comprises a groove formed in a distal portion of said delivery catheter.

9. An implantable pacing lead system for pacing a patient's heart, comprising:

a delivery catheter;

an elongated insulative lead body locatable in said delivery catheter and taking the form of a single non-diverging filament having a proximal end and a distal end;

a first electrode mounted to a distal portion of the lead body; and an active fixation device mounted fixedly to and extending laterally from the lead body proximal to the first electrode and longitudinally spaced from the first electrode, locatable within the delivery catheter, wherein said lead body comprises means for providing torsional rigidity extending between said active fixation device and the proximal end of the lead body, and wherein said lead has greater torsional rigidity proximal to said active fixation device than distal to said active fixation device.

10. An implantable pacing lead system for pacing a patient's heart, comprising:

a delivery catheter;

an elongated insulative lead body locatable in said delivery catheter and taking the form of a single non-diverging filament having a proximal end and a distal end;

a first electrode mounted to a distal portion of the lead body; and an active fixation device mounted fixedly to and extending laterally from the lead body proximal to the first electrode and longitudinally spaced from the first electrode, locatable within the delivery catheter, wherein said first electrode and said active fixation device are spaced from one another a sufficient distance to allow placement of said active fixation device in a patient's right atrium or superior vena cava while said first electrode is located adjacent tissue of a chamber of the patient's heart other than the right atrium;

wherein said lead body comprises means for providing torsional rigidity extending between said active fixation device and the proximal end of the lead body and wherein said lead has greater torsional rigidity proximal to said active fixation device than distal to said active fixation device.

11. A lead system according to claim 10 wherein said first electrode and said active fixation device are spaced from one another a sufficient distance to allow placement of said active fixation device in a patient's right atrium or superior vena cava while said first electrode is located adjacent tissue of a ventricle of the patients' heart.

12. A lead system according to claim 1 or claim 6 or claim 9 or claim 10 wherein said lead body is provided with a pre-formed curve located distal to said active fixation device.

13. A lead system according to claim 12 wherein said first electrode is located along said pre-formed curve.

14. A lead according to claim 12 wherein said first electrode is located distal to said pre-formed curve.

15. An implantable pacing lead system for pacing a patient's heart, comprising:

a delivery catheter;

an elongated insulative lead body locatable in said delivery catheter and taking the form of a single non-diverging filament having a proximal end and a distal end;

a first electrode mounted to a distal portion of the lead body; and an active fixation device mounted fixedly to and extending laterally from the lead body proximal to the first electrode and longitudinally spaced from the first electrode, locatable within the delivery catheter, wherein said lead body is provided with a pre-formed curve located distal to said active fixation device;

wherein said lead body comprises means for providing torsional rigidity extending between said active fixation device and the proximal end of the lead body and wherein said lead has greater torsional rigidity proximal to said active fixation device than distal to said active fixation device.

16. A lead system according to claim 15 wherein said first electrode is located along said pre-formed curve.

17. A lead according to claim 15 wherein said first electrode is located distal to said pre-formed curve.

18. A lead system according to claim 6 or claim 9 or claim 10 or claim 15 wherein the first electrode is a pacing electrode.

19. A lead system according to claim 6 or claim 9 or claim 10 or claim 15 wherein the first electrode is a cardioversion/defibrillation electrode.

20. A lead system according to claim 6 or claim 9 or claim 10 or claim 15, comprising a second electrode.

21. A lead system according to claim 20 wherein said active fixation device is said second electrode.

22. A lead system according to claim 20 wherein said active fixation device is adjacent said second electrode.

23. A lead system according to claim 20 wherein said active fixation device is longitudinally spaced from said second electrode.

24. A lead system according to claim 23 wherein said active fixation device is located distal to said second electrode.

25. A lead system according to claim 23 wherein said active fixation device is located proximal to said second electrode.

26. A lead system according to claim 9 or claim 10 or claim 15 wherein said delivery catheter comprises means for engaging said active fixation device.

27. A lead system according to claim 26 wherein said engaging means comprises a groove formed in a distal portion of said delivery catheter.

28. A lead system according to claim 1 or claim 9 or claim 10 or claim 15 wherein said delivery catheter is a deflectable catheter.

* * * * *